United States Patent
Chu et al.

[19]

[11] Patent Number: 5,882,316
[45] Date of Patent: Mar. 16, 1999

[54] MINIMALLY INVASIVE BIOPSY DEVICE

[75] Inventors: David Z. J. Chu; Todd McCarty, both of Pasadena, Calif.

[73] Assignee: City of Hope, Duarte, Calif.

[21] Appl. No.: 705,940

[22] Filed: Aug. 29, 1996

[51] Int. Cl.⁶ .................................................. A61B 10/00
[52] U.S. Cl. ....................... 600/567; 600/562; 600/564; 606/185
[58] Field of Search .................................. 128/748, 751, 128/753, 754, 757; 606/39, 45, 167, 185, 184; 604/165; 600/567, 562, 564, 566

[56] References Cited

U.S. PATENT DOCUMENTS

| | | | |
|---|---|---|---|
| 3,007,471 | 11/1961 | McClure, Jr. ............................ | 128/754 |
| 3,336,916 | 8/1967 | Edlich ..................................... | 128/754 |
| 4,007,732 | 2/1977 | Kvavle et al. . | |
| 4,099,518 | 7/1978 | Baylis et al. . | |
| 4,177,797 | 12/1979 | Baylis et al. . | |
| 4,682,606 | 7/1987 | DeCaprio ................................ | 600/567 |
| 4,850,373 | 7/1989 | Zatloukal et al. . | |
| 4,926,877 | 5/1990 | Bookwalter ............................. | 128/754 |
| 5,111,828 | 5/1992 | Kornberg et al. ...................... | 600/567 |
| 5,133,360 | 7/1992 | Spears .................................... | 128/754 |
| 5,353,804 | 10/1994 | Kornberg et al. . | |
| 5,380,277 | 1/1995 | Phillips ................................... | 606/45 |
| 5,449,357 | 9/1995 | Zinnanti ................................. | 606/45 |
| 5,462,062 | 10/1995 | Rubinstein et al. . | |
| 5,477,862 | 12/1995 | Haaga . | |
| 5,488,958 | 2/1996 | Topel et al. ............................. | 600/567 |
| 5,499,989 | 3/1996 | LaBash . | |
| 5,573,008 | 11/1996 | Robinson et al. ..................... | 600/567 |
| 5,578,030 | 11/1996 | Levin ..................................... | 606/39 |
| 5,595,186 | 1/1997 | Rubinstein et al. ................... | 128/754 |

OTHER PUBLICATIONS

Auto Suture Company; "The World's Most Advanced Alternative To Open Breast Surgery Offered Only By USSC"; 1996.

*Primary Examiner*—Richard J. Apley
*Assistant Examiner*—Justine R. Yu
*Attorney, Agent, or Firm*—Rothwell, Figg, Ernst & Kurz

[57] ABSTRACT

A minimally invasive biopsy device includes a cylindrical retractor and a cylindrical cutting tool slidingly engaged within the cylindrical retractor. The cylindrical retractor is adapted for insertion in an incision above a lesion to be excised, and separates the walls of the incision to provide access to the tissue to be excised. The cylindrical cutting tool has a cutting means which makes a cylindrical incision around the tissue to be excised. The tissue can then be accurately and quickly removed.

2 Claims, 3 Drawing Sheets

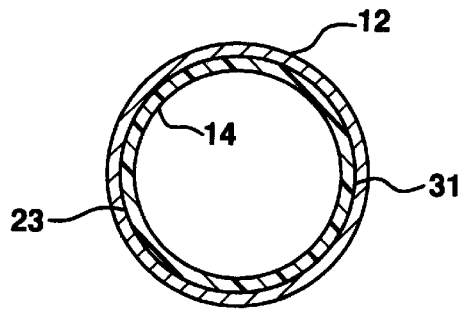
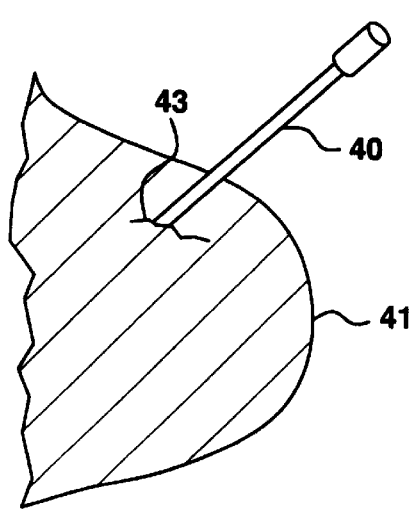
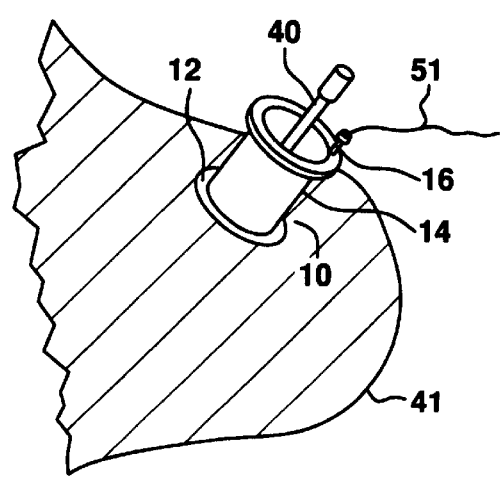
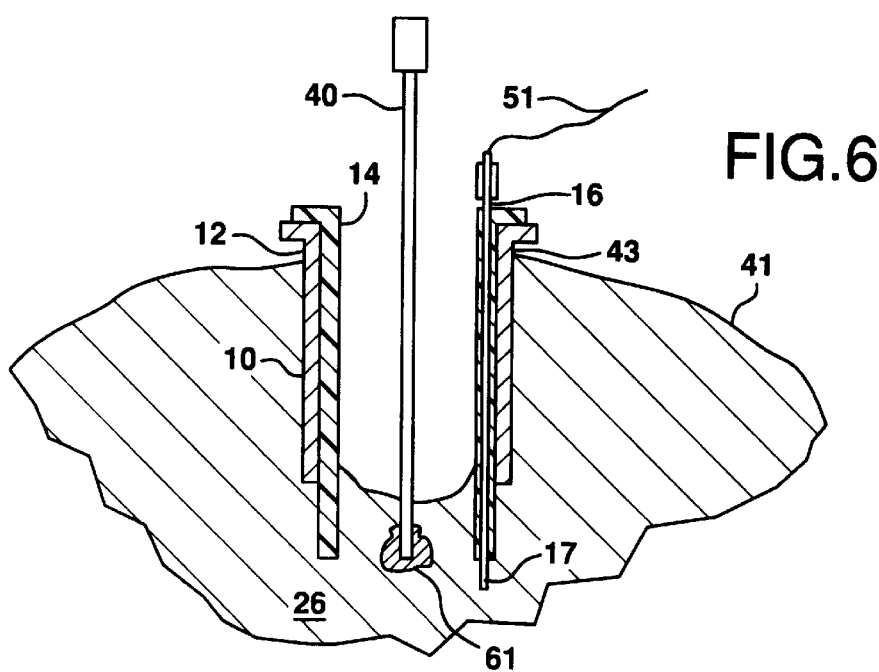

MINIMALLY INVASIVE BIOPSY DEVICE

BACKGROUND OF THE INVENTION

1. Field of the Invention

This invention relates to a surgical device for obtaining biopsies of soft tissue. More particularly, the invention relates to a minimally invasive biopsy device and a method for its use. The device of this invention is especially useful for obtaining biopsies of small breast tumors. In addition to being useful for diagnostic biopsies, the device of this invention may also be used for therapeutic removal of small malignant or benign tumors, a procedure sometimes referred to as "lumpectomy."

2. Description of Background Art

Early detection of breast cancer greatly improves a patient's prognosis. With the increasing use of mammography, ultrasound and other diagnostic procedures in preventive medicine, breast tumor biopsies are becoming a common surgical procedure. It is estimated that nearly two hundred thousand breast biopsies are performed in the United States each year.

Breast tumors are often detected during a routine mammographic examination. An occult lesion which is too small to be detected by palpation may be detected by mammography. While mammography provides a means for detecting and locating such lesions, it does not provide any meaningful indication of whether the abnormal tissue contains malignant or benign cells. Currently, such a diagnosis can only be accomplished by histologic examination of surgically removed tissue.

A variety of techniques exist for taking a breast biopsy. A needle or core biopsy involves inserting a biopsy needle (e.g., a Travenol Tru-Cut needle) into the lesion and removing a small amount of tissue for examination. This procedure has certain disadvantages, including the possibility of false-negative diagnoses as a consequence of obtaining too small a sample. Consequently, physicians often prefer to excise a small (i.e., less than about 1.5 cm in diameter) lesion completely. Indeed, when such a lesion is excised, it is esirable to include a 1–2 cm margin of tissue around the lesion to minimize the chances that any abnormal cells will have been missed and as a clear margin for treatment of malignancy.

Although small breast tumors can be detected radiologically, they are often difficult or impossible for the surgeon to locate during a biopsy procedure without some type of mechanical aid. Techniques have been developed to assist the surgeon in locating the tumor. For example, a needle may be inserted into the mammary tissue, with its end precisely placed in or near the abnormal tissue. Placement of the needle is accomplished using mammography or ultrasound. The patient is then moved to the surgical suite with the needle in place. The needle guides the surgeon to the area to be biopsied. A related technique involves the use of a thin wire having a barb or anchor on its end. The barb or anchor is placed in or near the lesion, with the aid or mammography or ultrasound, and the wire extends through the skin. The surgeon is guided to the location of the tumor by the wire. This latter technique is described by Kvavle et al. in U.S. Pat. No. 4,007,732.

Various devices have been developed to assist the surgeon in obtaining a percutaneous biopsy. For example, Baylis et al., U.S. Pat. No. 4,177,797, Haaga et al., U.S. Pat. No. 5,477,862 and Kornberg et al., U.S. Pat. No. 5,353,804 describe variations of a biopsy device that employs a stylus or pointed element surrounded by a cylindrical cutting tool. The stylus serves to penetrate the tissue and locate the instrument near the lesion. The biopsy is then obtained by sliding the outer cylindrical cutting tool along the stylus and beyond its point so as to make a cylindrical incision around the lesion. U.S. Pat. No. 4,007,732 describes a biopsy device which consists of a cylindrical cup-shaped cutting tool attached to a hollow shaft. A guide wire that is anchored in the lesion is passed through the shaft of the device and serves to guide the device to the lesion. The utility of these devices appears to be limited to obtaining diagnostic biopsies.

Notwithstanding such devices, the standard breast biopsy procedure remains the freehand technique in which the surgeon makes an incision with a scalpel and removes a roughly spherical mass of tissue using a scalpel, scissors and/or an electrocautery device. The freehand technique suffers from several disadvantages. First, incisions must be relatively large, which results in unnecessary scarring and the possibility of post-operative complications. Second, freehand surgery takes a relatively long time—on the order of 20–40 minutes—adding to the expense of the procedure and the risk of complications resulting from anesthesia. Third, freehand surgery is attended by a small but significant risk of missing a portion of the lesion.

There is, therefore, a need for a biopsy device that overcomes these disadvantages and which also can be employed for therapeutic removal of a small tumor in a single operation.

SUMMARY OF THE INVENTION

In accordance with this invention, a minimally invasive biopsy device for excising a soft tissue lesion along with a margin of tissue around the lesion comprises (a) a cylindrical retractor having a distal end to be inserted into an incision and a proximal end to extend out of the incision, and (b) a cylindrical cutting tool that is slidingly engaged within the cylindrical retractor, said cylindrical retractor having a length sufficient to allow its distal end to be placed within a distance from the lesion that is substantially equal to the margin while allowing the proximal end to extend out of the incision and having an inside diameter sufficient to accept the cylindrical cutting tool;

said cylindrical cutting tool having a cutting means on its distal end and having a length that is sufficient to allow the distal cutting means to be extended beyond the lesion by a distance equal to the margin, while allowing the proximal end to remain at least substantially even with the proximal end of the cylindrical retractor and having a diameter substantially equal to the diameter of the lesion plus the margins on each side of the lesion.

BRIEF DESCRIPTION OF THE DRAWINGS

FIG. 3 is a transverse cross-sectional view of the device taken along lines 3—3 of FIG. 1.

FIG. 4 is an illustration of a human breast having a lesion-locating needle in place and showing an incision for placement of the minimally invasive biopsy device of this invention.

FIG. 5 is a further illustration of the human breast illustrated in FIG. 4, showing the cylindrical retractor of the minimally invasive biopsy device of this invention inserted into the incision.

FIG. 6 is a cross-sectional view of the human breast illustrated in FIGS. 4 and 5, showing the cylindrical retractor in place in the incision and showing the cylindrical cutting tool inserted around the lesion.

DETAILED DESCRIPTION OF THE INVENTION

The minimally invasive biopsy device of this invention is described, by reference to the drawings, in connection with a preferred embodiment. Those skilled in the art will appreciate that variations and modifications to the device may be made without departing from the invention as defined by the claims. Moreover, the device has been described in connection with the obtaining of breast biopsies, however it will be recognized that it can be used for taking biopsies of a wide variety of soft tissues, e.g., the liver. In addition, the device can be used for therapeutic as well as diagnostic excision of tissue.

Figure 1:
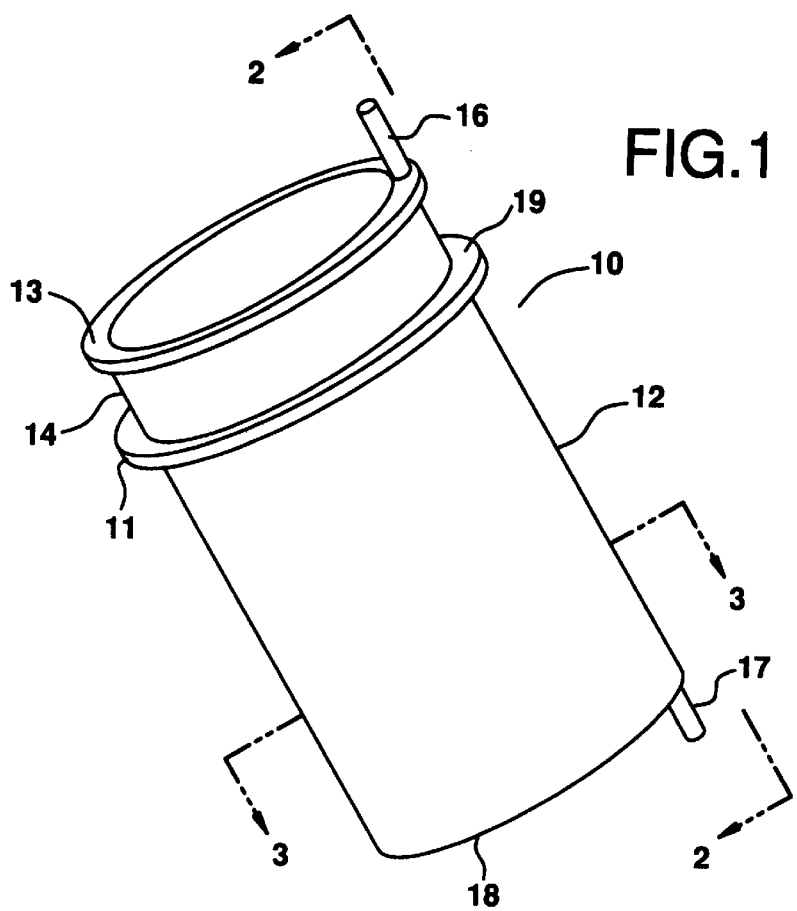
FIG. 1 is a perspective view of the minimally invasive biopsy device of this invention.
Figure 2:
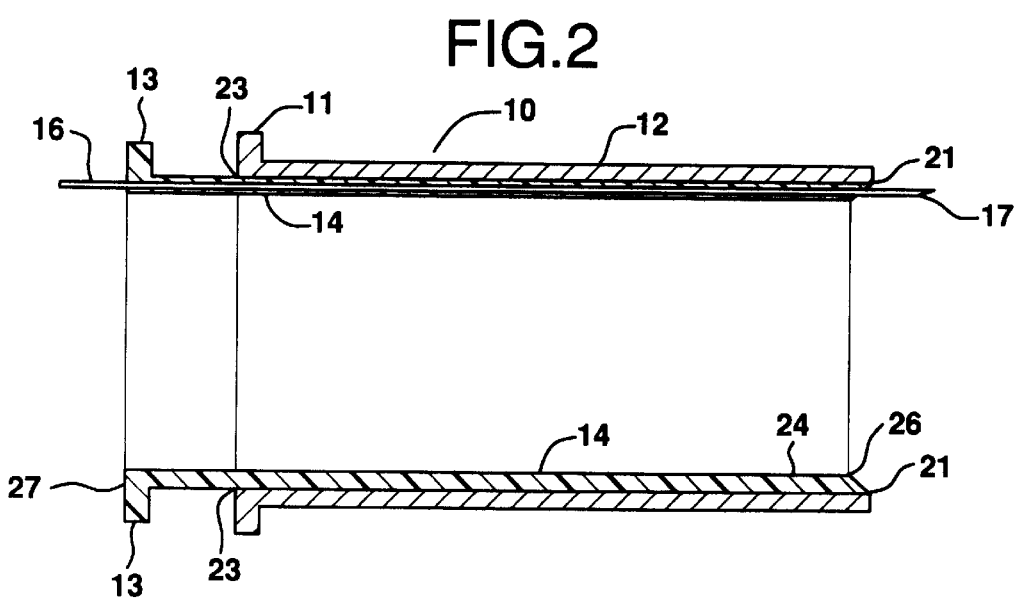
FIG. 2 is a longitudinal cross-sectional view of the device taken along lines 2—2 of FIG. 1.

Referring to FIG. 1, the minimally invasive biopsy device 10 has a cylindrical retractor 12 and a cylindrical cutting tool 14. As shown in FIGS. 1, 2 and 3, the cylindrical cutting tool 14 is slidingly engaged within the cylindrical retractor 12. Advantageously, the fit between the cutting tool and the retractor is such as to allow facile movement of one relative to the other, but is sufficiently snug to prevent tissue from passing between the two elements.

FIG. 3 is a transverse cross-sectional view of the biopsy device taken along lines 3—3 of FIG. 1.

The cylindrical retractor has a distal end 18 and a proximal end 19. The proximal end may have a lip 11 which provides structural reinforcement and which rests on the skin to provide a physical barrier preventing the proximal end 19 of retractor 12 from sliding into an incision.

Referring to FIG. 2, the cylindrical cutting tool 14 has a distal end 26 and a proximal end 27. The cylindrical cutting tool 14 also advantageously has a lip 13, which prevents the proximal end 27 from sliding beyond the proximal end 19 of cylindrical retractor 12 and which facilitates the surgeon's grasp of the device. A cutting means is positioned on the distal end 26 of cylindrical cutting tool 14. A preferred cutting means is a Bovie electrocautery tip 17 which extends beyond distal end 26 and which is supplied with electrical current by a conductive rod or wire 16 which passes through the wall of cylindrical cutting tool 14. Alternatively, the cutting means may be a sharpened edge 21 around the entire circumference of cylindrical cutting tool 14. Sharpened edge 21 permits the tool to make a cylindrical incision when forced into soft tissue. In another embodiment, the cutting means may comprise a sharpened knife edge (not shown) extending out of distal end 26 in a manner similar to electrocautery tip 17. Distal end 26 is illustrated in the drawings as a sharpened edge; however, when the cutting means is an electrocautery tip or a knife edge, distal end 26 preferably is blunt.

Referring to FIG. 2, the length of cutting tool 14 advantageously is greater than that of cylindrical retractor 12. As will be apparent from the description of the use of the minimally invasive biopsy device provided below, the length of cylindrical cutting tool 14, including that of the cutting means, is sufficient to permit a cylindrical incision to extend by about the distance of one margin beyond the lesion to be removed. For example, if the lesion is about 1 cm in diameter and it is desired to leave margins of 1 cm all around the lesion, then the the cylindrical retractor 12 will be advanced to a depth appropriate to achieve a 1 cm margin and cylindrical cutting tool 14, including the cutting means, preferably has a length sufficient to permit it to extend approximately 3 cm beyond the distal end of surgical retractor 12. Although, the cylindrical cutting tool 14 can be removed and the surgical excision carried out to the desired depth by the operative technique.

Similarly, the inside diameter of cylindrical cutting tool 14 is advantageously approximately equal to the diameter of the lesion plus the margins on each side of the lesion. For example, for a 1 cm lesion, the inside diameter of cylindrical cutting tool 14 is about 2 cm, assuming that it is desired to leave margins of about 0.5 cm.

The minimally invasive biopsy device of this invention may be provided in different sizes so that the surgeon can select a size which will allow complete excision of the lesion along with the desired margins, while not unnecessarily removing an excess of tissue. Typical sizes are 2 and 3 cm in diameter and 4 and 6 cm in length, respectively. Two or three sizes of the device will accommodate most breast biopsy situations.

The embodiment depicted in the drawings further includes a conductive rod 16 which extends through the wall of cylindrical cutting tool 14. The conductive rod 16 terminates at its distal end with an electrocautery tip 17. The conductive rod 16 is preferably slidingly engaged in the wall of cutting tool 14, so that electrocautery tip 17 can be retracted and extended. In addition to serving as a cutting means, electrocautery tip 17 can be used to seal bleeding vessels during cutting with cutting tool 14.

Cylindrical retractor 12, including lip 11, serves both to retract tissue, thus providing access to the lesion and surrounding margins to be removed and to protect healthy tissue against accidental electrocautery injury. It also compresses surrounding tissue, thus reducing bleeding.

Figure 8:
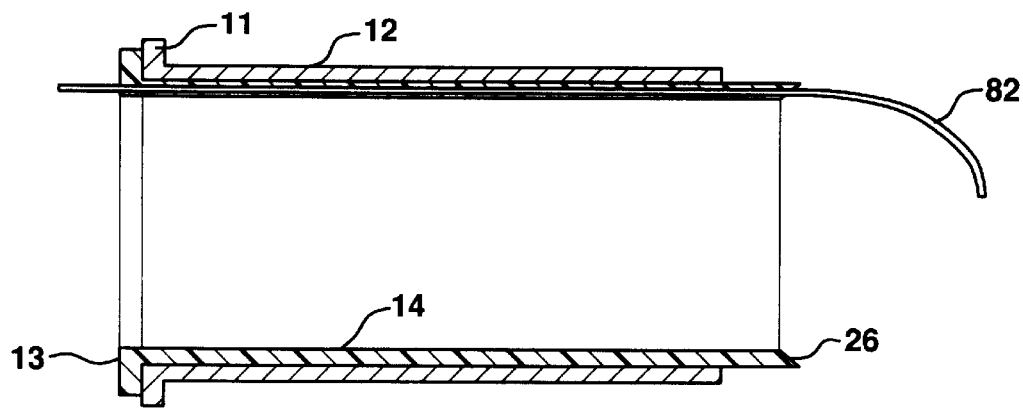
FIG. 8 is a cross-sectional view of an alternative embodiment of the minimally invasive biopsy device of this invention, in which a retractable curved electrocautery tip is provided to facilitate excision of the biopsy tissue.

Referring to FIG. 8, the electrocautery tip 82 may be curved to facilitate excising the biopsy tissue. In this embodiment, the conductive rod and electrocautery tip 82 is made of a resilient metal, such as spring steel, so that it can be retracted into the wall of cylindrical cutting tool 14, and, when extended, it assumes the curved shape. In this embodiment, the electrocautery tip and conductive rod advantageously have sufficient length that, when fully extended, distal amputation of the specimen is achieved. In this embodiment as well as in the embodiments shown in FIGS. 1–7, the conductive rod may be coated with an insulating material so that cutting is only effected by the electrocautery tip.

The use of the minimally invasive biopsy device of this invention is illustrated in FIGS. 4–7. FIG. 4 shows a human breast 41 in which a tumor or abnormal tissue mass has been detected by mammography or other means. A locater needle 40 has been inserted into the breast tissue, with the embedded end of the needle placed in the abnormal tissue with the help of mammography. FIG. 4 shows an incision 43, which has a length slightly longer than the diameter of the lesion plus the desired margins on each side of the lesion. The depth of the incision is such that it terminates approximately one margin length above the lesion. (See FIG. 6.)

FIG. 5 shows the minimally invasive biopsy device 10 inserted into the incision, with the locater needle 40 still in place. Cylindrical retractor 12 has been placed into the incision 43, retracting the walls of the incision to provide unobstructed access to the tissue to be removed. In FIG. 5, cylindrical cutting tool 14 has not yet been moved into the tissue. Electrical current is provided to conductive rod 16 by means of wire 51. While the drawings illustrate the biopsy device in a coaxial position relative to locater needle 40, it will be appreciated that the locater needle can be perpendicular or at other angles relative to the biopsy device.

FIG. 6 is a cross-sectional view of breast 41 with minimally invasive biopsy device 10 in place in incision 43. Cylindrical retractor 12 has retracted the tissue to a depth about one margin length above the lesion 61 to be removed. Cylindrical cutting device 14 makes a cylindrical incision by forcing it downward, and rotating it to facilitate tissue cutting. Cutting is stopped when distal end 26 of cutting tool 14 is about one margin length below lesion 61.

Figure 7:
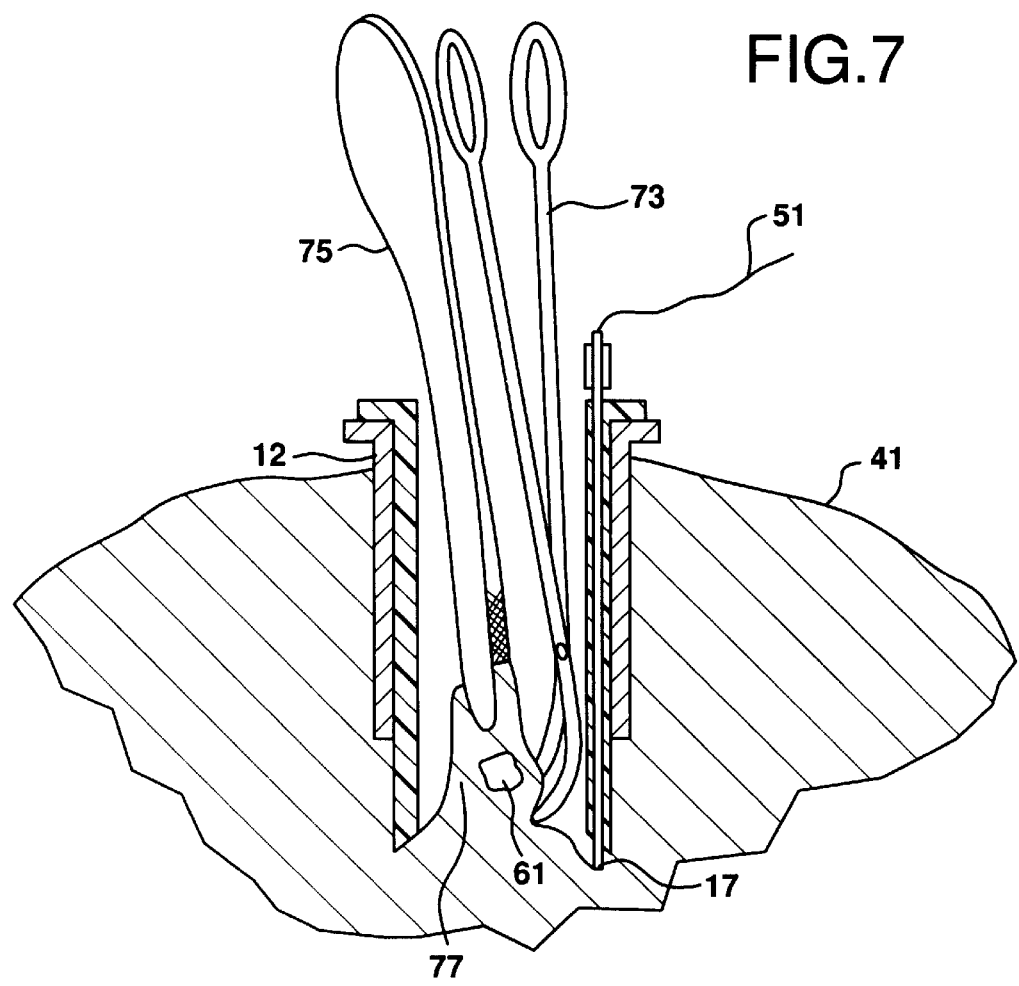
FIG. 7 is a further cross-sectional view of the human breast illustrated in FIG. 6, showing the use of forceps to apply traction to the tissue to be biopsied and showing curved surgical scissors being used to excise the tissue.

At this point, the locater needle 40 is removed, and the cylindrical tissue plug, which contains lesion 61 and appropriate margins of tissue all around the lesion, is removed. The removal of the tissue may be accomplished by conventional surgical techniques, as illustrated in FIG. 7, which shows traction being applied with forceps 75 and excision being effected with curve-tipped surgical scissors (e.g., Mayo scissors) 73. Alternatively, if the embodiment depicted in FIG. 8 is employed, the curved electrocautery tip 82 may be extended and energized, and the tissue excised by rotating cylindrical cutting tool 14 360°. After removing the biopsy tissue, it may be submitted to a pathology laboratory for examination. The minimally invasive biopsy device may be removed from the incision, which is then closed by standard surgical procedures.

The minimally invasive biopsy device of this invention is simple in construction and easy to use. It may be constructed of any suitable material, preferably plastic. This device facilitates complete excision of the lesion and margins with an accuracy that is difficult to achieve using conventional surgical techniques. Compared to conventional biopsy, surgery times have been reduced by about 50%, incisions have been reduced by 10% to 50%, specimen sizes have been reduced, and lesion retrieval rate has improved.

The minimally invasive biopsy device of this invention may be modified to provide further conveniences to the surgeon. For example, traction and suction devices may be built into the device, and a sharp cutting tip may be used in place of or in addition to the electrocautery tip. Other modifications will occur to those skilled in the art.

We claim:

1. A method for excising a lesion and a tissue margin around the lesion, which comprises:

(a) making an incision above the lesion, said incision having a length greater than a diameter of a lesion plus a selected length of tissue margin on each side of the lesion, and a depth which terminates at a distance above the lesion substantially equal to the selected length of tissue margin;

(b) inserting into the incision a cylindrical retractor having a distal end and a proximal end, said retractor having an inside diameter at least approximately equal to the diameter of the lesion plus the selected length of tissue margin on each side of the lesion, said cylindrical retractor having a length which allows the proximal end of the retractor to extend out of the incision when the distal end is placed at the bottom of the incision;

(c) slidingly engaging a cylindrical cutting tool into the cylindrical retractor, said cylindrical cutting tool having a proximal end that extends out of the cylindrical retractor and a distal end that extends into the cylindrical retractor, said distal end of the cylindrical cutting tool having a cutting means; and said cylindrical cutting tool having an inside diameter approximately equal to the diameter of the lesion to be removed plus the selected length of tissue margin on each side of the lesion, said cylindrical cutting tool, including the cutting means, having a length sufficient to permit a cylindrical incision made by the cutting means which extends a selected distance beyond the lesion to be removed, the selected distance beyond the lesion being substantially equal to a length of a selected tissue margin;

(d) inserting the cylindrical cutting tool into the tissue to make a cylindrical incision around the lesion and the tissue margins to be excised;

(e) surgically removing the lesion and the tissue margins around the lesion.

2. The method of claim 1 which further comprises making at least a portion of the incision in step (d) using an electrocautery tip which extends beyond the distal end of the cylindrical cutting tool and which is provided with electrical current by a conductive rod that passes through the wall of the cylindrical cutting tool.

* * * * *